US011529516B2

(12) United States Patent
López-Poveda

(10) Patent No.: US 11,529,516 B2
(45) Date of Patent: Dec. 20, 2022

(54) MEDIAL OLIVOCOCHLEAR REFLEX SOUND CODING WITH BANDWIDTH NORMALIZATION

(71) Applicant: Universidad de Salamanca, Salamanca (ES)

(72) Inventor: Enrique Alejandro López-Poveda, Salamanca (ES)

(73) Assignee: Universidad De Salamanca, Salamanca (ES)

( * ) Notice: Subject to any disclaimer, the term of this patent is extended or adjusted under 35 U.S.C. 154(b) by 0 days.

(21) Appl. No.: 16/619,162

(22) PCT Filed: Jun. 28, 2018

(86) PCT No.: PCT/US2018/039896
§ 371 (c)(1),
(2) Date: Dec. 4, 2019

(87) PCT Pub. No.: WO2019/006059
PCT Pub. Date: Jan. 3, 2019

(65) Prior Publication Data
US 2020/0197703 A1    Jun. 25, 2020

Related U.S. Application Data

(60) Provisional application No. 62/525,902, filed on Jun. 28, 2017.

(51) Int. Cl.
*A61N 1/36* (2006.01)
*A61N 1/02* (2006.01)
*A61N 1/05* (2006.01)

(52) U.S. Cl.
CPC ......... *A61N 1/36038* (2017.08); *A61N 1/025* (2013.01); *A61N 1/0541* (2013.01); *A61N 1/36167* (2013.01); *A61N 1/36039* (2017.08)

(58) Field of Classification Search
CPC ................ A61N 1/36036; A61N 1/36038
See application file for complete search history.

(56) References Cited

U.S. PATENT DOCUMENTS

2012/0303093 A1  11/2012  Wouters et al.
2016/0375422 A1  12/2016  Schleich et al.

FOREIGN PATENT DOCUMENTS

EP    2942976    * 11/2015
WO    WO 2016/089936 A1    6/2016

OTHER PUBLICATIONS

International Searching Authority/EP, International Search Report and Written Opinion of the International Searching Authority, Application No. PCT/US2018/039896, dated Oct. 10, 2018, 16 pages.

* cited by examiner

*Primary Examiner* — George R Evanisko
(74) *Attorney, Agent, or Firm* — Sunstein LLP

(57) ABSTRACT

A signal processing arrangement is described for signal processing in a bilateral hearing implant system. A channel compression module develops a inhibition-adjusted band pass signal for each band pass signal using a channel-specific dynamic inhibition adjustment based on a channel-normalized medial olivocochlear reflex model that reflects bandwidth energy for a corresponding contralateral band pass signal and bandwidth energy for a selected reference contralateral band pass signal.

15 Claims, 5 Drawing Sheets

MEDIAL OLIVOCOCHLEAR REFLEX SOUND CODING WITH BANDWIDTH NORMALIZATION

This application is a 371 national phase entry of Patent Cooperation Treaty Application PCT/US2018/039896, filed Jun. 28, 2018, and also claims priority from U.S. Provisional Patent Application 62/525,902, filed Jun. 28, 2017, which is incorporated herein by reference in its entirety.

FIELD OF THE INVENTION

The present invention relates to hearing implant systems, and more specifically, to techniques for producing electrical stimulation signals in such systems.

BACKGROUND ART

A normal ear transmits sounds as shown in FIG. 1 through the outer ear 101 to the tympanic membrane 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolus where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, hearing prostheses have been developed. For example, when the impairment is related to operation of the middle ear 103, a conventional hearing aid may be used to provide mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system, including an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110.

Typically, the electrode array 110 includes multiple electrode contacts 112 on its surface that provide selective stimulation of the cochlea 104. Depending on context, the electrode contacts 112 are also referred to as electrode channels. In cochlear implants today, a relatively small number of electrode channels are each associated with relatively broad frequency bands, with each electrode contact 112 addressing a group of neurons with an electric stimulation pulse having a charge that is derived from the instantaneous amplitude of the signal envelope within that frequency band.

In some coding strategies, stimulation pulses are applied at a constant rate across all electrode channels, whereas in other coding strategies, stimulation pulses are applied at a channel-specific rate. Various specific signal processing schemes can be implemented to produce the electrical stimulation signals. Signal processing approaches that are well-known in the field of cochlear implants include continuous interleaved sampling (CIS), channel specific sampling sequences (CSSS) (as described in U.S. Pat. No. 6,348,070, incorporated herein by reference), spectral peak (SPEAK), and compressed analog (CA) processing.

FIG. 2 shows the major functional blocks in a typical cochlear implant signal processing system wherein band pass signals are processed and coded to generate electrode stimulation signals to stimulation electrodes in an implanted cochlear implant electrode array. For example, commercially available Digital Signal Processors (DSP) can be used to perform speech processing according to a 12-channel CIS approach. The initial acoustic audio signal input is produced by one or more sensing microphones, which may be omni-directional and/or directional. Filter Bank 201 pre-processes the initial acoustic audio signal with a bank of multiple band pass filters, each of which is associated with a specific band of audio frequencies—for example, a digital filter bank having 12 digital Butterworth band pass filters of 6th order, Infinite Impulse Response (IIR) type—so that the acoustic audio signal is filtered into some M band pass signals, $B_1$ to $B_M$ where each signal corresponds to the band of frequencies for one of the band pass filters. Each output of the CIS band pass filters can roughly be regarded as a sinusoid at the center frequency of the band pass filter which is modulated by the signal envelope. This is due to the quality factor ($Q \approx 3$) of the filters. In case of a voiced speech segment, this envelope is approximately periodic, and the repetition rate is equal to the pitch frequency. Alternatively and without limitation, the Filter Bank 201 may be implemented based on use of a fast Fourier transform (FFT) or a short-time Fourier transform (STFT). Based on the tonotopic organization of the cochlea, each electrode contact in the scala tympani often is associated with a specific band pass filter of the external filter bank.

FIG. 3 shows an example of a short time period of an audio speech signal from a microphone, and FIG. 4 shows an acoustic microphone signal decomposed by band-pass filtering by a bank of filters into a set of signals. An example of pseudocode for an infinite impulse response (IIR) filter bank based on a direct form II transposed structure is given by Fontaine et al., *Brian Hears: Online Auditory Processing Using Vectorization Over Channels*, Frontiers in Neuroinformatics, 2011; incorporated herein by reference in its entirety:

```
for j = 0 to number of channels − 1 do
    for s = 0 to number of samples − 1 do
        Y_j(s) = B_{0j} * X_j(s) + Z_{0j}
        for i = 0 to order− 3 do
            Z_{ij} = B_{i+1,j} * X_j(s) + Z_{i+1,j} −A_{i+1,j} * Y_j(s)
        end for
        Z_{order−2,j} = B_{order− 1,j} * X_j(s) −A_{order−1,j} * Y_j(s)
    end for
end for
```

The band pass signals $B_1$ to $B_M$ (which can also be thought of as frequency channels) are input to a Signal Processor 202 which extracts signal specific stimulation information—e.g., envelope information, phase information, timing of requested stimulation events, etc.—into a set of N stimulation channel signals $S_1$ to $S_N$ that represent electrode specific requested stimulation events. For example, channel specific sampling sequences (CSSS) may be used as described in U.S. Pat. No. 6,594,525, which is incorporated herein by reference in its entirety. For example, the envelope extraction may be performed using 12 rectifiers and 12 digital Butterworth low pass filters of 2nd order, IIR-type.

A Pulse Timing and Coding Module 203 applies a nonlinear mapping function (typically logarithmic) to the amplitude of each band-pass envelope. This mapping function—for example, using instantaneous nonlinear compression of the envelope signal (map law)—typically is adapted to the needs of the individual cochlear implant user during fitting of the implant in order to achieve natural loudness growth. This may be in the specific form of functions that are applied to each requested stimulation event signal $S_1$ to $S_N$ that reflect patient-specific perceptual characteristics to produce a set of electrode stimulation signals $A_1$ to $A_M$ that provide an optimal electric representation of the acoustic signal. A logarithmic function with a form-factor c typically may be applied as a loudness mapping function, which typically is identical across all the band pass analysis channels. In different systems, different specific loudness mapping functions other than a logarithmic function may be used, with just one identical function applied to all channels or one individual function for each channel to produce the electrode stimulation signals $A_1$ to $A_M$ outputs from the Pulse Timing and Coding Module 203.

A Pulse Generation Module 204 develops the set of electrode stimulation signals $A_1$ to $A_M$ into a set of output electrode pulses $E_1$ to $E_M$ for the electrode contacts in the implanted electrode array which stimulate the adjacent nerve tissue. The output electrode pulses $E_1$ to $E_M$ may be symmetrical biphasic current pulses with amplitudes that are directly obtained from the compressed envelope signals.

In the specific case of a CIS system, the stimulation pulses are applied in a strictly non-overlapping sequence. Thus, as a typical CIS-feature, only one electrode channel is active at a time and the overall stimulation rate is comparatively high. For example, assuming an overall stimulation rate of 18 kpps, where kpps stands for thousand stimulation pulses per second, and a 12 channel filter bank, the stimulation rate per channel is 1.5 kpps. Such a stimulation rate per channel usually is sufficient for adequate temporal representation of the envelope signal. The maximum overall stimulation rate is limited by the minimum phase duration per pulse. The phase duration cannot be arbitrarily short because, the shorter the pulses, the higher the current amplitudes have to be to elicit action potentials in neurons, and current amplitudes are limited for various practical reasons. For an overall stimulation rate of 18 kpps, the phase duration is 27 µs, which is near the lower limit.

In the CIS strategy, the signal processor only uses the band pass signal envelopes for further processing, i.e., they contain the entire stimulation information. For each electrode channel, the signal envelope is represented as a sequence of biphasic pulses at a constant repetition rate. A characteristic feature of CIS is that the stimulation rate is equal for all electrode channels and there is no relation to the center frequencies of the individual channels. It is typical that the pulse repetition rate is not a temporal cue for the patient (i.e., it should be sufficiently high so that the patient does not perceive tones with a frequency equal to the pulse repetition rate). The pulse repetition rate is usually chosen at greater than twice the bandwidth of the envelope signals (based on the Nyquist theorem).

Another cochlear implant stimulation strategy that does transmit fine time structure information is the Fine Structure Processing (FSP) strategy by Med-El. Zero crossings of the band pass filtered time signals are tracked, and at each negative to positive zero crossing, a Channel Specific Sampling Sequence (CSSS) is started. Typically, CSSS sequences are only applied on the first one or two most apical electrode channels, covering the frequency range up to 200 or 330 Hz. The FSP arrangement is described further in Hochmair I, Nopp P, Jolly C, Schmidt M, Schößer H, Garnham C, Anderson I, *MED-EL Cochlear Implants: State of the Art and a Glimpse into the Future*, Trends in Amplification, vol. 10, 201-219, 2006, which is incorporated herein by reference.

In addition to the specific processing and coding approaches discussed above, different specific pulse stimulation modes are possible to deliver the stimulation pulses with specific electrodes—i.e. mono-polar, bi-polar, tri-polar, multi-polar, and phased-array stimulation. And there also are different stimulation pulse shapes—i.e. biphasic, symmetric triphasic, asymmetric triphasic pulses, or asymmetric pulse shapes. These various pulse stimulation modes and pulse shapes each provide different benefits; for example, higher tonotopic selectivity, smaller electrical thresholds, higher electric dynamic range, less unwanted side-effects such as facial nerve stimulation, etc. But some stimulation arrangements are quite power consuming, especially when neighboring electrodes are used as current sinks. Up to 10 dB more charge might be required than with simple mono-polar stimulation concepts (if the power-consuming pulse shapes or stimulation modes are used continuously).

Bilateral stimulation has long been used in hearing aids, but it has only recently become common in hearing implants such as cochlear implants (CI). For cochlear implants, binaural stimulation requires a bilateral implant system with two implanted electrode arrays, one in each ear. The incoming left and right side acoustic signals are similar to those in hearing aids and may simply be the output signals of microphones located in the vicinity of the left and right ear, respectively. Bilateral cochlear implants provide the benefits of two-sided hearing which can allow a listener to localize sources of sound in the horizontal plane. Two-sided hearing also is known to make speech easier to understand in noise. This is explained more fully, for example, in Bronkhorst, A. W., and Plomp, R., *The Effect Of Head-Induced Interaural Time And Level Differences On Speech Intelligibility In Noise*, J. Acoust. Soc. Am. 83, 1508-1516, 1988, which is incorporated herein by reference.

It is also known that for natural hearing, the central nervous system controls sound coding in the cochlea via medial olivocochlear (MOC) efferents. MOC efferents innervate outer hair cells in the cochlea, the activation of which inhibits the motion of the basilar membrane for low- and moderate-level sounds. This inhibitory effect restores the dynamic range of individual auditory nerve fibers in noise and possibly increases the proportion of nerve fibers that discharge within their dynamic range. Presumably this improves the neural representation of transient sound features and thus facilitates speech recognition and sound localization in noise. For further details, refer to Guinan J J., *Cochlear efferent innervation and function*. Curr. Opin. Otolaryngol. Head & Neck Surgery, 18 (2010), pp. 447-453; which is incorporated herein by reference. It might also magnify spatial release from masking, see for example Kim S. H., Frisina R. D., Frisina D. R. *Effects of age on speech understanding in normal hearing listeners: Relationship between the auditory efferent system and speech intelligibility in noise*. Speech Communication (2006) 48, 862.

CI users have greater difficulty understanding speech in noise than listeners with normal hearing. This may be partly due to their lacking the antimasking benefits of the medial olivocochlear (MOC) reflex, and the hearing-in-noise capacity of CI users may be improved with sound processing strategies that mimic MOC effects on compression. See Patent Cooperation Treaty Publication WO 2015/169649; Lopez-Poveda et al., *Roles of the contralateral efferent reflex in hearing demonstrated with cochlear implants*, Adv. Exp. Med. Biol. 894, 105-114, 2016; and Lopez-Poveda et al., *A bilateral sound coding strategy inspired by the contralateral medial olivocochlear reflex*, Ear Hear. 37, e138-e148, 2016; all of which are incorporated herein by reference in their entireties. On the other hand, the ability of CI users to recognize speech in noise can be thought to concomitantly depend on the effective speech-to-noise ratio (SNR) at the output of the CI audio processor and on the sensitivity of the CI user to the corresponding electrical stimulation.

SUMMARY OF THE INVENTION

Embodiments of the present invention are directed to a signal processing arrangement and corresponding method for a bilateral hearing implant system having left side and right side hearing implants. Each hearing implant includes at least one sensing microphone configured for sensing a sound environment to develop a corresponding microphone signal output. A filter bank is configured for processing the microphone signal to generate multiple band pass signals, wherein each band pass signal represents an associated band of audio frequencies. A channel compression module is configured to develop an inhibition-adjusted band pass signal for each band pass signal using a channel-specific dynamic inhibition based on a channel-normalized medial olivocochlear reflex model reflecting bandwidth energy for a corresponding contralateral band pass signal and bandwidth energy for a selected reference contralateral band pass signal. A pulse timing and coding module is configured for processing the inhibition-adjusted band pass signals to develop stimulation timing signals. And a pulse generation module is configured for processing the stimulation timing signals to develop electrode stimulation signals for the hearing implant for perception as sound.

In further specific embodiments, the medial olivocochlear reflex model may specifically be configured to produce larger channel-specific dynamic inhibition adjustments for lower frequency band pass signals. The channel inhibition module may be configured to use a channel-specific dynamic inhibition adjustment function $$= \frac{\ln(1 + c \cdot x)}{\ln(1 + c)},$$

where x represents amplitude of the input band pass signal, y represents amplitude of the adjusted band pass signal, and c is a dynamically determined inhibition factor that determines amount of the inhibition adjustment. In such embodiments, x and y may range within an interval [0, 1], and/or the dynamically determined inhibition factor c and the bandwidth energy for the corresponding contralateral band pass signal may be inversely related such that the greater the bandwidth energy for the corresponding contralateral band pass signal, the smaller the value of the dynamically determined inhibition factor c. The bandwidth energy for the corresponding contralateral band pass signal may be based on root mean square output amplitude integrated over a preceding exponentially decaying time window with two time constants, $\tau_a$ and $\tau_b$. And the pulse timing and coding module may be configured to use a continuous interleaved sampling (CIS) or Channel Specific Sampling Sequences (CSSS) based or Fine Structure Processing (FSP) coding strategy or a combination thereof to develop the stimulation timing signals.

DETAILED DESCRIPTION OF SPECIFIC EMBODIMENTS

According to some embodiments of the invention a user wears two cochlear implants, one in each ear, with corresponding sound processors capable of exchanging time-varying signals.

Previous signal processing arrangements that used a medial olivocochlear reflex (MOCR) model, were based on a inhibition parameter c for each band pass channel that depended on output energy E from the corresponding contralateral band pass channel. For broadband signals, the resulting contralateral inhibition could have been greater for higher frequency channels than for lower frequency channels because high-frequency channels were broader in frequency and may have contained more energy than lower frequency channels. Embodiments of the present invention address that problem for binaural CI sound coding using a channel-specific dynamic inhibition adjustment based on a channel-normalized MOCR model that reflects bandwidth energy for a corresponding contralateral band pass signal and bandwidth energy for a selected reference contralateral band pass signal.

Figure 1:
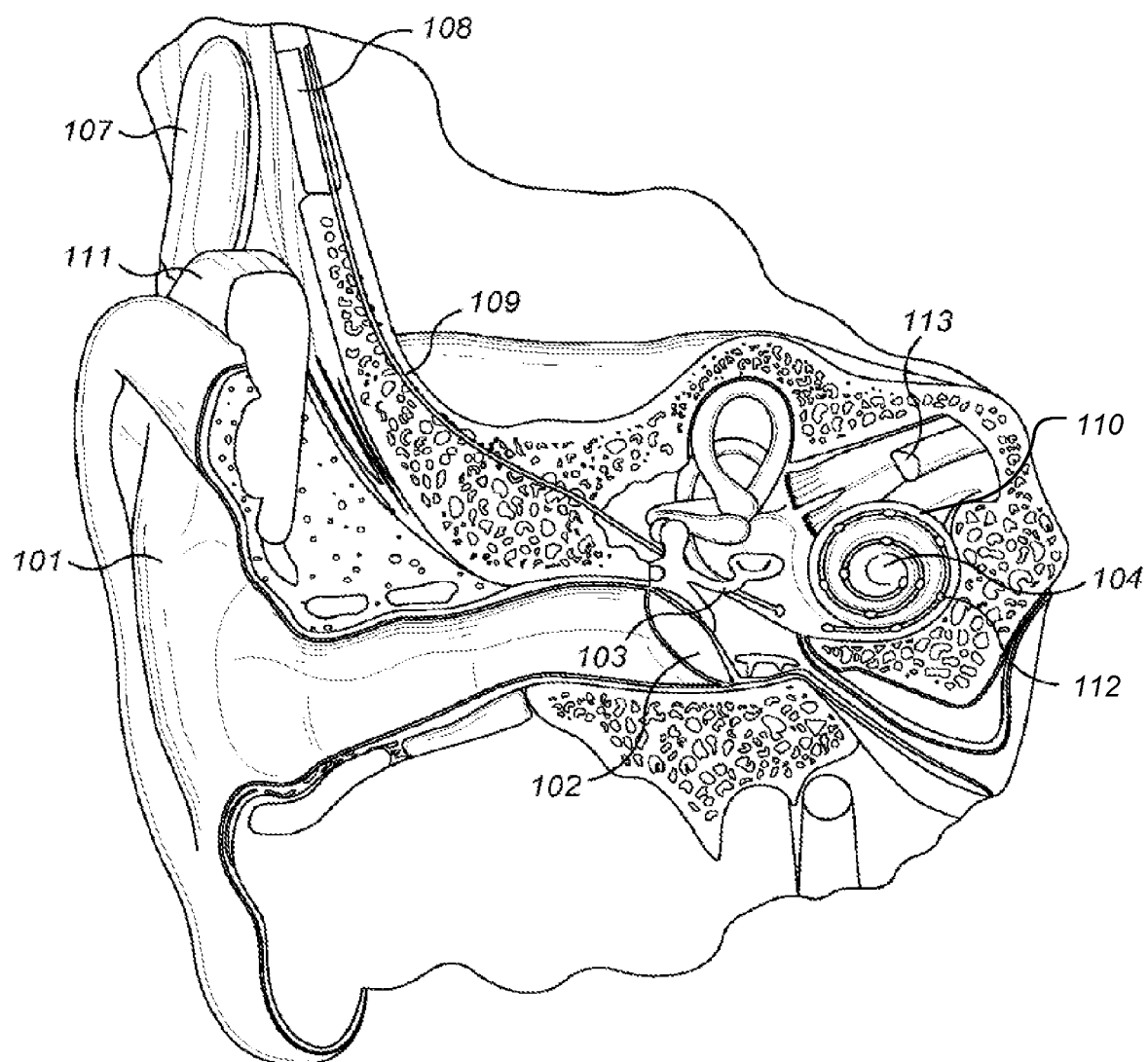
FIG. 1 shows a section view of a human ear with a typical cochlear implant system designed to deliver electrical stimulation to the inner ear.
Figure 2:
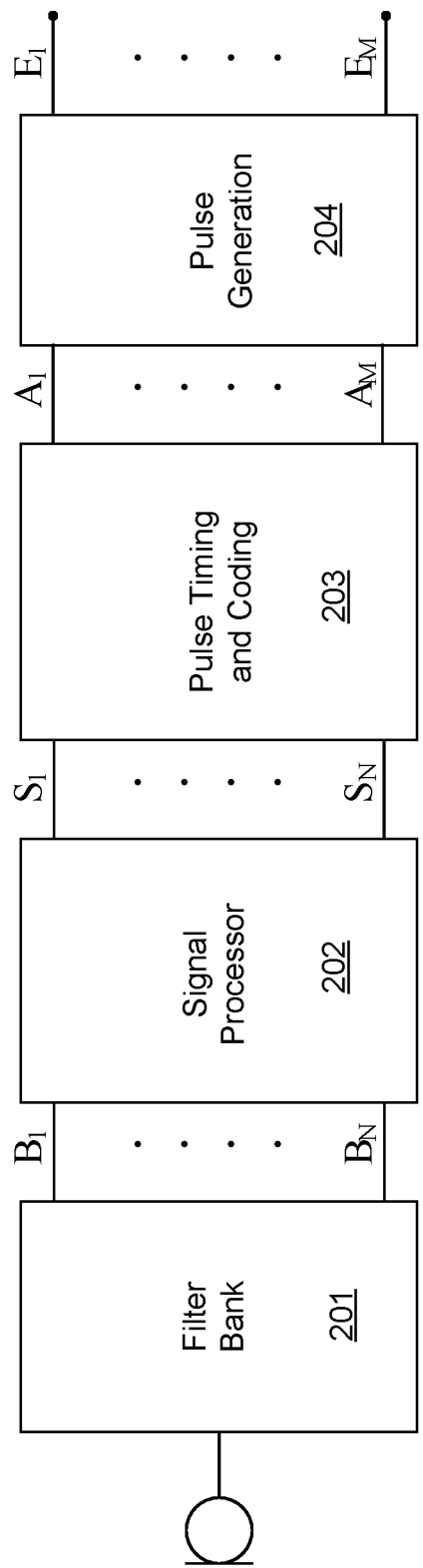
FIG. 2 shows various functional blocks in a continuous interleaved sampling (CIS) processing system.
Figure 3:
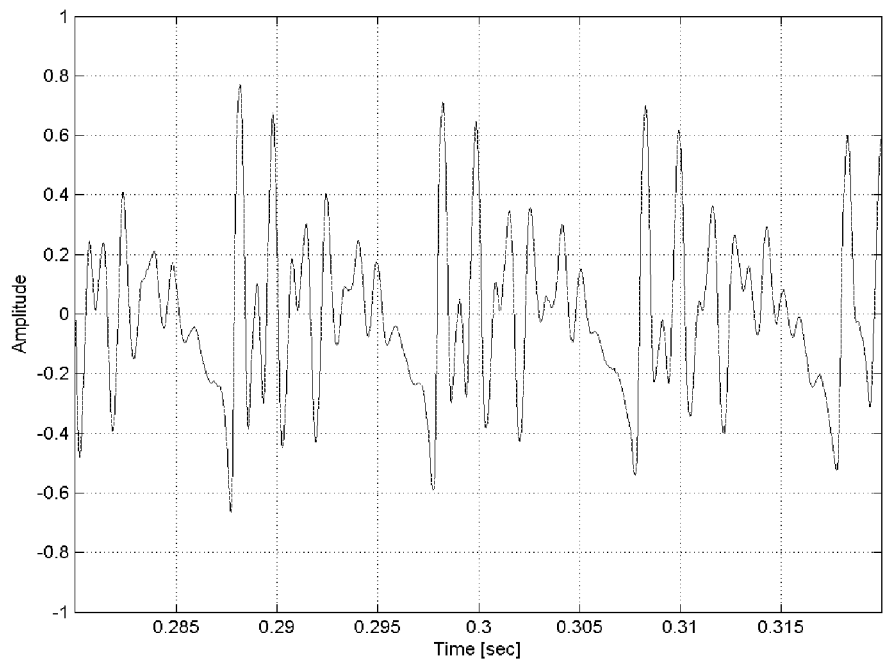
FIG. 3 shows an example of a short time period of an audio speech signal from a microphone.
Figure 4:
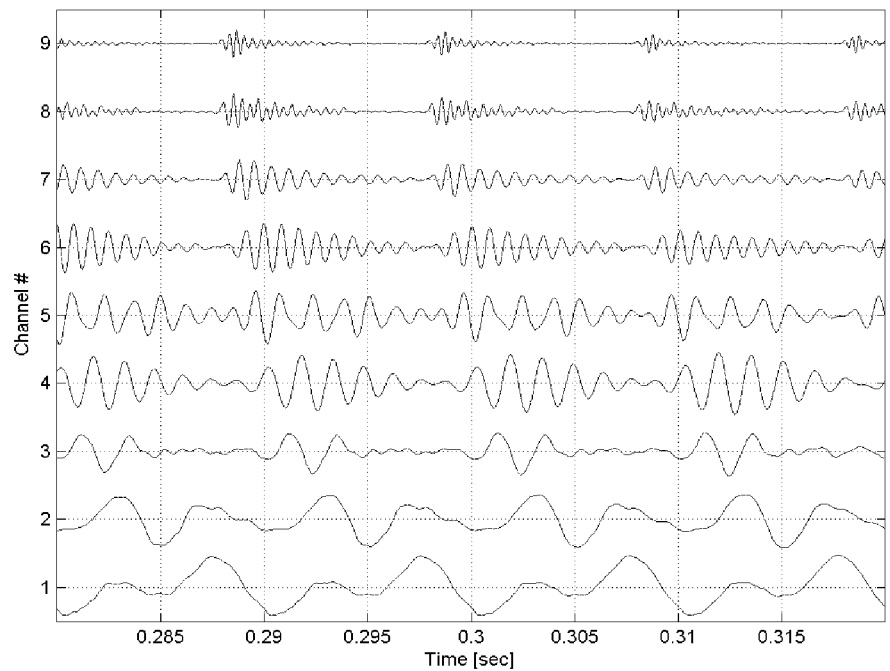
FIG. 4 shows an acoustic microphone signal decomposed by band-pass filtering by a bank of filters into a set of signals.
Figure 5:
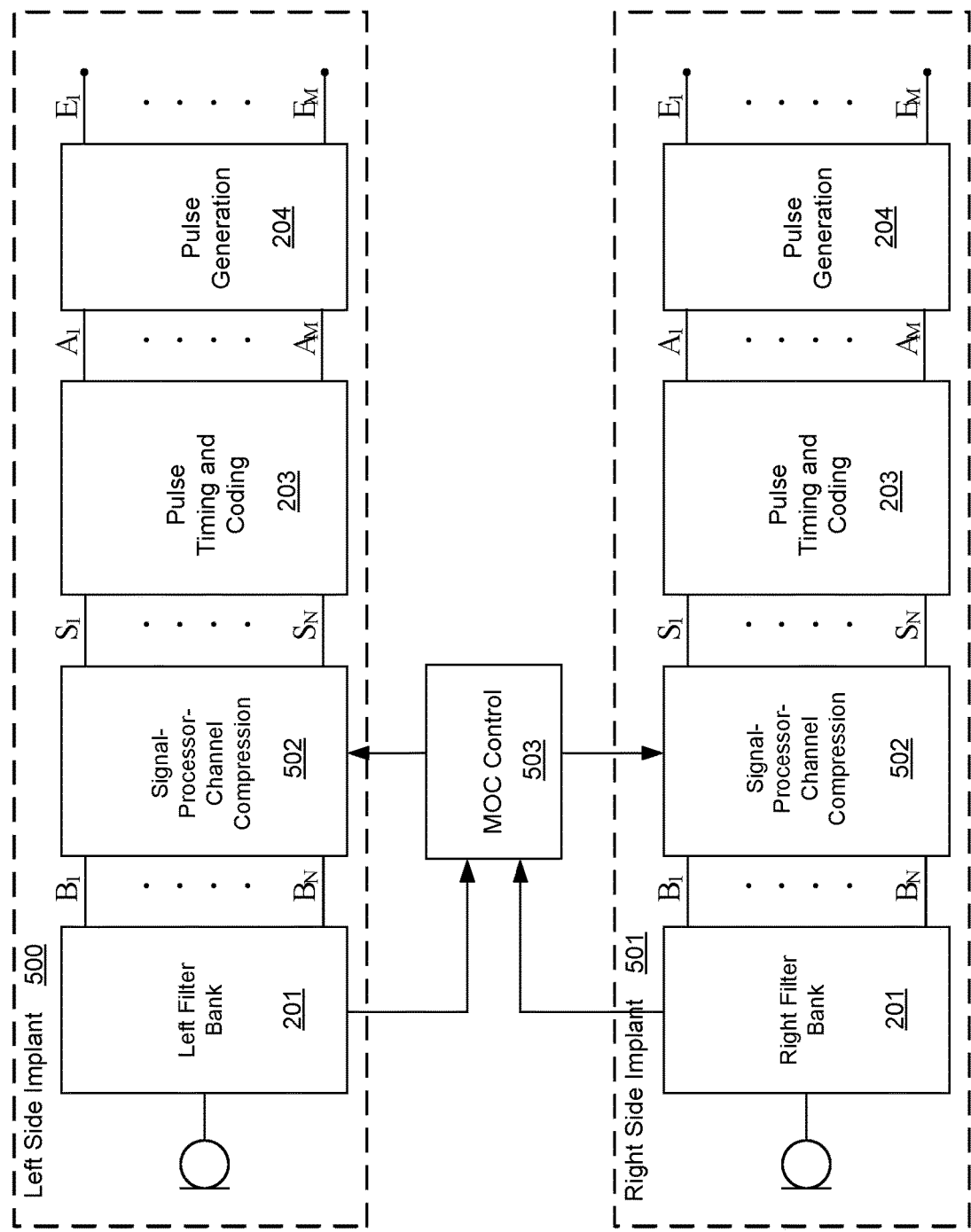
FIG. 5 shows various functional blocks in a system for signal processing according to an embodiment of the present invention.
Figure 6:
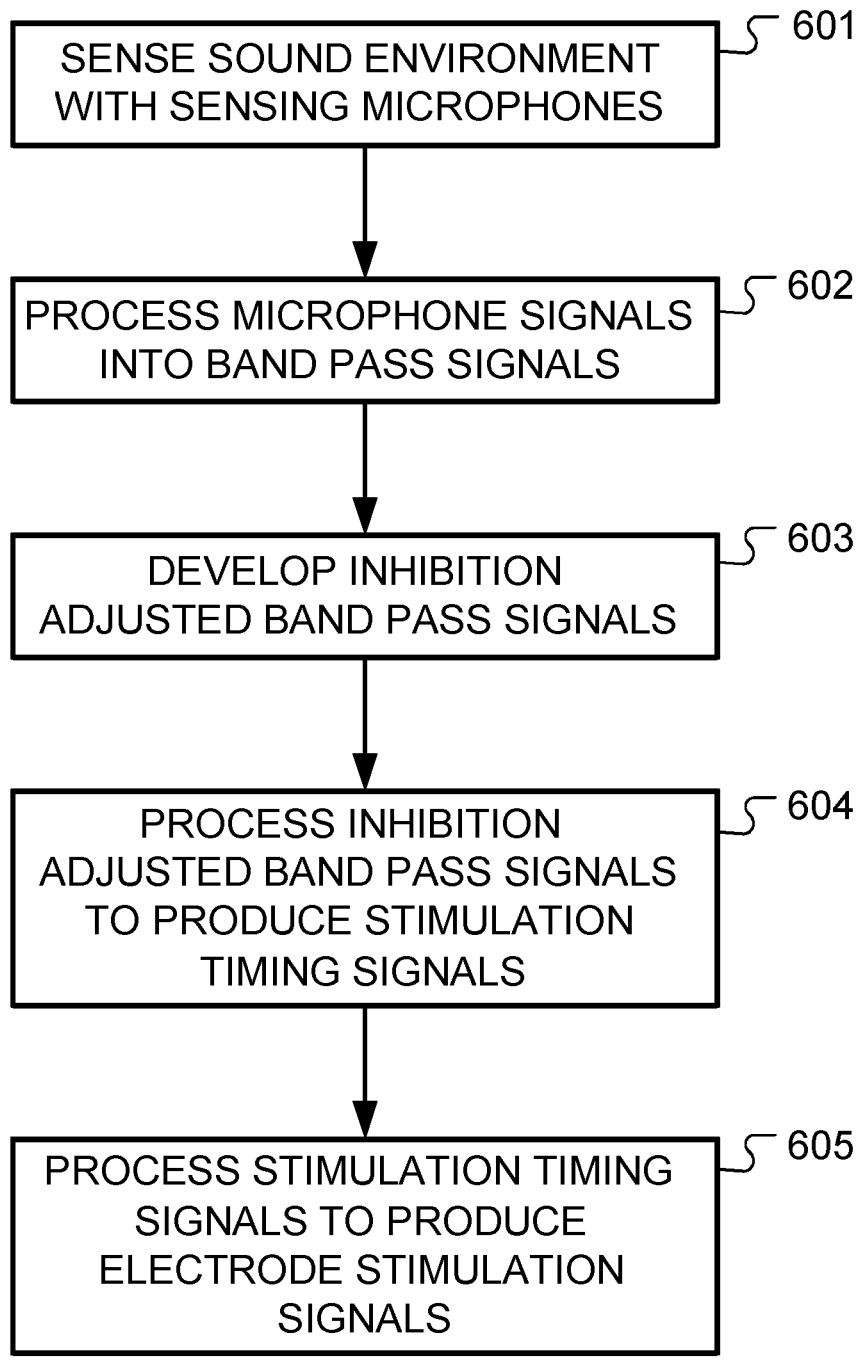
FIG. 6 shows various logical blocks in a method for signal processing according to an embodiment of the present invention.

FIG. 5 shows various functional blocks in a system, and FIG. 6 shows various logical blocks in a method, for signal processing according to embodiments of the present invention for a bilateral hearing implant system having a left side hearing implant 500 and a right side hearing implant 501. The system shown in FIG. 5 is based on the system discussed above with respect to FIG. 2 for CIS-based sound coding. So on each side there initially is at least one sensing microphone configured for sensing a sound environment to develop a corresponding microphone signal output, step 601, that is processed by a Filter Bank 201, step 602, to generate multiple band pass signals $B_1$ to $B_M$ (which can also be thought of as frequency channels), each representing an associated band of audio frequencies. For example, the Filter Bank 201 might specifically include a high-pass pre-emphasis filter such as a first-order Butterworth filter with a 3-dB cutoff frequency of 1.2 kHz, followed by a bank of 12 sixth-order Butterworth band-pass filters with 3-dB cutoff frequencies that follow a modified logarithmic distribution between 100 and 8500 Hz.

A Signal Processor-Channel Compression Module 502 then processes the band pass signals $B_1$ to $B_M$ as described above with respect to FIG. 2 (e.g., performing envelope extraction via full-wave rectification and low-pass filtering using a fourth-order Butterworth low-pass filter with a 3-dB cutoff frequency of 400 Hz) and additionally performing a channel-specific dynamic logarithmic inhibition adjustment, step 603, as discussed more fully below that is based on a channel-normalized medial olivocochlear reflex model to produce adjusted band pass signals $S_1$ to $S_N$.

Pulse Timing and Coding Module 203 then applies pulse coding (e.g., using a continuous interleaved sampling (CIS) coding strategy) and a non-linear mapping function as described above, step 604, to the adjusted band pass signals $S_1$ to $S_N$ to produce a set of electrode stimulation signals $A_1$ to $A_M$ that the Pulse Generation Module 204 develops into the output electrode pulses $E_1$ to $E_M$, step 605, for the electrode contacts in the implanted electrode array.

MOC Module 503 applies the channel-normalized medial olivocochlear reflex model to the band pass signals $B_1$ to $B_M$ from each Filter Bank 201 for the Signal Processor-Channel Compression Module 502 to perform the channel-specific dynamic inhibition adjustment in step 603, which may specifically be configured to produce larger channel-specific dynamic inhibition adjustments for lower frequency band pass signals. For example, this may be based on a channel-specific dynamic inhibition adjustment function $$y = \frac{\ln(1 + c \cdot x)}{\ln(1 + c)},$$

where x represents amplitude of the input band pass signal, y represents amplitude of the adjusted band pass signal, and c is a dynamically determined inhibition factor that determines amount of the inhibition adjustment. For further details, refer to the discussion in Boyd P J, *Effects of programming threshold and maplaw settings on acoustic thresholds and speech discrimination with the MED-EL COMBI 40+ cochlear implant*. Ear Hear. 27, 608-618, 2006; which is incorporated herein by reference in its entirety. In another example the channel-specific dynamic inhibition adjustment function $y=ax^p+k$, where x represents amplitude of the input band pass signal, y represents amplitude of the adjusted band pass signal, k a constant, and p is a dynamically determined inhibition factor that determines amount of the inhibition adjustment. It is however understood, that the invention is not limited to these two dynamic inhibition adjustment functions, but other suitable functions may be used. More formally, inhibition factor c (or p) is controlled using the output energy E, normalized to the channel bandwidth E':

$$E' = E \cdot \left(\frac{BW_{ref}}{BW}\right)^{0.5}$$

where BW is the channel bandwidth, and $BW_{ref}$ is a reference channel bandwidth.

In a typical embodiment, x and y may range within an interval [0, 1]. The dynamically determined inhibition factor c and the bandwidth energy for the corresponding contralateral band pass signal may be inversely related such that the greater the bandwidth energy for the corresponding contralateral band pass signal, the smaller the value of the dynamically determined inhibition factor c. For example, the relationship between the instantaneous value of c and the instantaneous contralateral output energy may be such that the greater the output energy, the smaller the value of c. In one example the relationship may be given by $$c(t) = \frac{c_a - c_b}{1 + \exp[-\alpha(E'(t) - \beta)]} + c_b$$

where $c_a$, $c_b$ and $\beta$ are constants and E' is the normalized instantaneous output energy E for a given time t, as described in Patent Cooperation Treaty Publication WO2015/169649 more detailed, incorporated herein by reference. In another example, the relationship may be given by $$\log_{10}(c(t)) = \frac{\log_{10}(c_a) - \log_{10}(c_b)}{1 + \exp[-\alpha(\log_{10}(E'(t)) - \log_{10}(\beta))]} + \log_{10}(c_b)$$

where $c_a$, $c_b$ and $\beta$ are constants and E' is the normalized instantaneous output energy E for a given time t. It is however understood, that the invention is not limited to these two functions, but other suitable functions may be used.

Specifically, c might vary between approximately 30 and 1000 for contralateral output energies of 0 and −20 dB full scale (FS; where 0 dB FS corresponds to peak amplitude at unity), respectively.

Based on the exponential time-course of activation and deactivation of the MOC effect (see, e.g., Backus and Guinan, *Time-course of the human medial olivocochlear reflex*, J. Acoust. Soc. Am. 119, 2889-2904, 2006; which is incorporated herein by reference in its entirety), the bandwidth energy for the corresponding contralateral band pass signal may be based on root mean square output amplitude integrated over a preceding exponentially decaying time window with two time constants, $\tau_a$ and $\tau_b$. For example, to reflect the time course of activation and deactivation of the natural MOCR, time constants might be set to $\tau_a$=2 ms and $\tau_b$=300 ms.

For example, in an embodiment where channels #1 and #12 are respectively the lowest and highest in frequency, overall inhibition will be greatest when $BW_{ref}$ equals the bandwidth of channel #12 ($BW_{\#12}$), and gradually decreases for lower number channels. Bandwidth normalizations that produce greater inhibition can compromise audibility and reduce intelligibility. In addition, for normal hearing listeners, it has been observed that a contralateral broadband noise at 60 dB SPL increases auditory thresholds by about 1 to 9 dB. The inventor has observed, that normalization with $BW_{ref}=BW_{\#6}$, $BW_{\#7}$, or $BW_{\#8}$ produces more reasonable overall inhibition, with effectively equal or greater inhibition in the lower than in the higher frequency channels without compromising audibility significantly.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A signal processing system for a bilateral hearing implant system, the system comprising:
   left side and right side hearing implants, configured to communicate signals to each other, each of the hearing implants having:
   at least one sensing microphone configured for sensing a sound environment and developing a corresponding microphone signal output,
   a filter bank configured for processing the microphone signal output to generate a plurality of band pass signals,
      wherein each of the plurality of band pass signals has an associated amplitude, an associated band of audio frequencies, an associated bandwidth, and an associated instantaneous output energy E,
      wherein each of the plurality of band pass signals of a given filter bank has a corresponding contralateral band pass signal received from the other hearing implant,
   a medial olivocochlear control module configured to determine for each of the plurality of band pass signals a normalized instantaneous output energy E', normalized based on a channel bandwidth of the corresponding contralateral bandpass signal and on a channel bandwidth of a selected reference contralateral band pass signal;
   a channel compression module configured to receive and process each of the plurality of band pass signals for the given hearing implant, and each of the normalized output energies from the plurality of contralateral band pass signals to develop an inhibition-adjusted band pass signal for each of the plurality of band pass signals, the channel compression module providing a channel-specific dynamic inhibition adjustment, in which the associated amplitude of each band pass signal is adjusted as a function of the normalized instantaneous output energy of the corresponding contralateral bandpass signal;
   a pulse timing and coding module configured for processing the inhibition-adjusted band pass signals and developing stimulation timing signals; and
   a pulse generation module configured for processing the stimulation timing signals and developing electrode stimulation signals for the given hearing implant for perception as sound.

2. The system according to claim 1, configured to produce the channel-specific dynamic inhibition adjustments such that they are equal or larger for the band pass signals of a lower frequency compared to the band pass signals of a higher frequency.

3. The system according to claim 1, wherein each of the channel compression modules is configured to provide the channel-specific dynamic inhibition adjustment used a dynamic inhibition adjustment function $$y = \frac{\ln(1 + c \cdot x)}{\ln(1 + c)},$$

where x represents the amplitude of the given band pass signal, y represents the amplitude of the inhibition adjusted band pass signal, and c is a channel-specific dynamically determined inhibition factor.

4. The system according to claim 3, wherein x and y range within an interval [0, 1].

5. The system according to claim 3, wherein the dynamically determined inhibition factor c and the instantaneous output energy for the corresponding contralateral band pass signal are inversely related such that the greater the instantaneous output energy for the corresponding contralateral band pass signal, the smaller the value of the dynamically determined inhibition factor c.

6. The system according to claim 1, wherein the instantaneous output energy for the corresponding contralateral band pass signal is a function of root mean square output amplitude integrated over a preceding exponentially decaying time window with two time constants, $\tau_a$ and $\tau_b$.

7. The system according to claim 1, wherein each of the pulse timing and coding modules is configured to use a continuous interleaved sampling (CIS) or Channel Specific Sampling Sequences (CSSS) based on Fine Structure Processing (FSP) coding strategy or a combination thereof to develop the stimulation timing signals.

8. The system according to claim 1 wherein each of the medial olivocochlear control modules is configured to determine the normalized instantaneous output energy from the equation $$E' = E\left(\frac{BW_{ref}}{BW}\right)^{0.5}$$

where E is equal to the instantaneous output energy of the corresponding contralateral bandpass signal, BW is the channel bandwidth of the corresponding contralateral bandpass signal and $BW_{ref}$ is the channel bandwidth of the selected reference contralateral band pass signal.

9. A method for signal processing in a bilateral hearing implant system having left side and right side hearing implants configured to communicate signals to each other, the method for each hearing implant comprising:

sensing a sound environment with at least one sensing microphone and developing a corresponding microphone signal output;

processing the microphone signal output with a filter bank to generate a plurality of band pass signals, wherein each of the plurality of band pass signals has an associated amplitude, an associated band of audio frequencies, an associated bandwidth, and an associated instantaneous output energy E, and wherein each of the plurality of band pass signals of a given filter bank has a corresponding contralateral band pass signal received from the other hearing implant;

determining, by using a medial olivocochlear control module, for each of the plurality of band pass signals, a normalized instantaneous output energy E', by normalizing based on a channel bandwidth of the corresponding contralateral bandpass signal, and on a channel bandwidth of a selected reference contralateral band pass signal;

receiving and processing with a channel compression module each of the plurality of band pass signals for the given hearing implant, and each of the normalized output energies from the plurality of contralateral band pass signals by applying channel-specific dynamic inhibition adjustments to each band pass signal of the plurality of band pass signals to develop an inhibition-adjusted band pass signal for each of the plurality of band pass signals, the channel-specific dynamic inhibition adjustments including adjusting the associated amplitude of each band pass signal as a function of the normalized instantaneous output energy;

processing the inhibition-adjusted band pass signals with a pulse timing and coding module and developing stimulation timing signals; and processing the stimulation timing signals with a pulse generation module and developing electrode stimulation signals for the hearing implant.

10. The method according to claim 9, wherein the channel-specific dynamic inhibition adjustments are equal or larger for the band pass signals of a lower frequency, compared to the band pass signals of a higher frequency.

11. The method according to claim 9, wherein each of the channel compression modules adjusts the amplitude of each band pass signal using a dynamic inhibition adjustment function $$y = \frac{\ln(1 + c \cdot x)}{\ln(1 + c)},$$

where x represents the amplitude of the given band pass signal, y represents the amplitude of the inhibition adjusted band pass signal, and c is a dynamically determined inhibition factor indicative of amount of the inhibition adjustment.

12. The method according to claim 11, wherein x and y range within an interval [0, 1].

13. The method according to claim 11, wherein the dynamically determined inhibition factor c and the instantaneous output energy for the corresponding contralateral band pass signal are inversely related such that the greater the instantaneous output energy for the corresponding contralateral band pass signal, the smaller the value of the dynamically determined inhibition factor c.

14. The method according to claim 9, wherein the instantaneous output energy for the corresponding contralateral band pass signal is a function of root mean square output amplitude integrated over a preceding exponentially decaying time window with two time constants, $\tau_a$ and $\tau_b$.

15. The method according to claim 9, wherein a continuous interleaved sampling (CIS) or Channel Specific Sampling Sequences (CSSS) based or Fine Structure Processing (FSP) coding strategy or a combination thereof is used by the pulse timing and coding module to develop the stimulation timing signals.

* * * * *